United States Patent
Sato

(10) Patent No.: US 11,331,224 B2
(45) Date of Patent: May 17, 2022

(54) PROCESSING DEVICE FOR ABSORBENT ARTICLE

(71) Applicant: ZUIKO CORPORATION, Osaka (JP)

(72) Inventor: Hitoshi Sato, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 266 days.

(21) Appl. No.: 16/758,319

(22) PCT Filed: Nov. 2, 2018

(86) PCT No.: PCT/JP2018/040851
§ 371 (c)(1),
(2) Date: Apr. 22, 2020

(87) PCT Pub. No.: WO2019/098060
PCT Pub. Date: May 23, 2019

(65) Prior Publication Data
US 2020/0315860 A1    Oct. 8, 2020

(30) Foreign Application Priority Data

Nov. 14, 2017    (JP) .............................. JP2017-218959

(51) Int. Cl.
*A61F 13/15* (2006.01)
*B26F 1/38* (2006.01)
*B26D 1/22* (2006.01)

(52) U.S. Cl.
CPC .. *A61F 13/15723* (2013.01); *A61F 13/15772* (2013.01); *B26D 1/225* (2013.01);
(Continued)

(58) Field of Classification Search
CPC .......... A61F 13/15723; A61F 13/15772; A61F 2013/15918; B26D 1/225; B26D 1/26;
(Continued)

(56) References Cited

U.S. PATENT DOCUMENTS

| 5,388,490 A * | 2/1995 | Buck ................... B26D 7/2628 |
| | | 83/887 |
| 2013/0160626 A1 | 6/2013 | Saga |
| 2017/0057157 A1 * | 3/2017 | Lebowitz ................ B29C 65/48 |

FOREIGN PATENT DOCUMENTS

| JP | 2007-229898 A | 9/2007 |
| JP | 2009-39341 A | 2/2009 |

(Continued)

OTHER PUBLICATIONS

International Search Report Issued in PCT/JP2018/040851 dated Dec. 11, 2018.

*Primary Examiner* — Linda L Gray
*Assistant Examiner* — Christopher C Caillouet
(74) *Attorney, Agent, or Firm* — Renner, Otto, Boisselle & Sklar, LLP

(57) ABSTRACT

An absorbent article processing device includes a cutter roll and an anvil roll. The cutter roll includes a roll main body; a blade protruding in a radial direction in a first angular range of a part of a circumferential direction of the roll main body; a first bearer protruding in the radial direction in a second angular range of a part of the circumferential direction including at least the first angular range and being in contact with the anvil roll, and being cut out in an angular range excluding the second angular range at a first end portion in an axial direction of the roll main body; and a second bearer provided around the entire circumference or a part of the circumferential direction and being in contact with the anvil roll at the second end portion in an axial direction of the roll main body.

12 Claims, 7 Drawing Sheets

(52) U.S. Cl.
CPC ............ *B26F 1/384* (2013.01); *B26F 1/3826* (2013.01); *A61F 2013/15918* (2013.01)

(58) Field of Classification Search
CPC .......... B26D 1/285; B26D 3/10; B26D 7/204; B26D 5/00; B26F 1/3826; B26F 1/384
See application file for complete search history.

(56) References Cited

FOREIGN PATENT DOCUMENTS

| | | |
|---|---|---|
| JP | 2012-19832 A | 2/2012 |
| JP | 2013-71809 A | 4/2013 |

\* cited by examiner

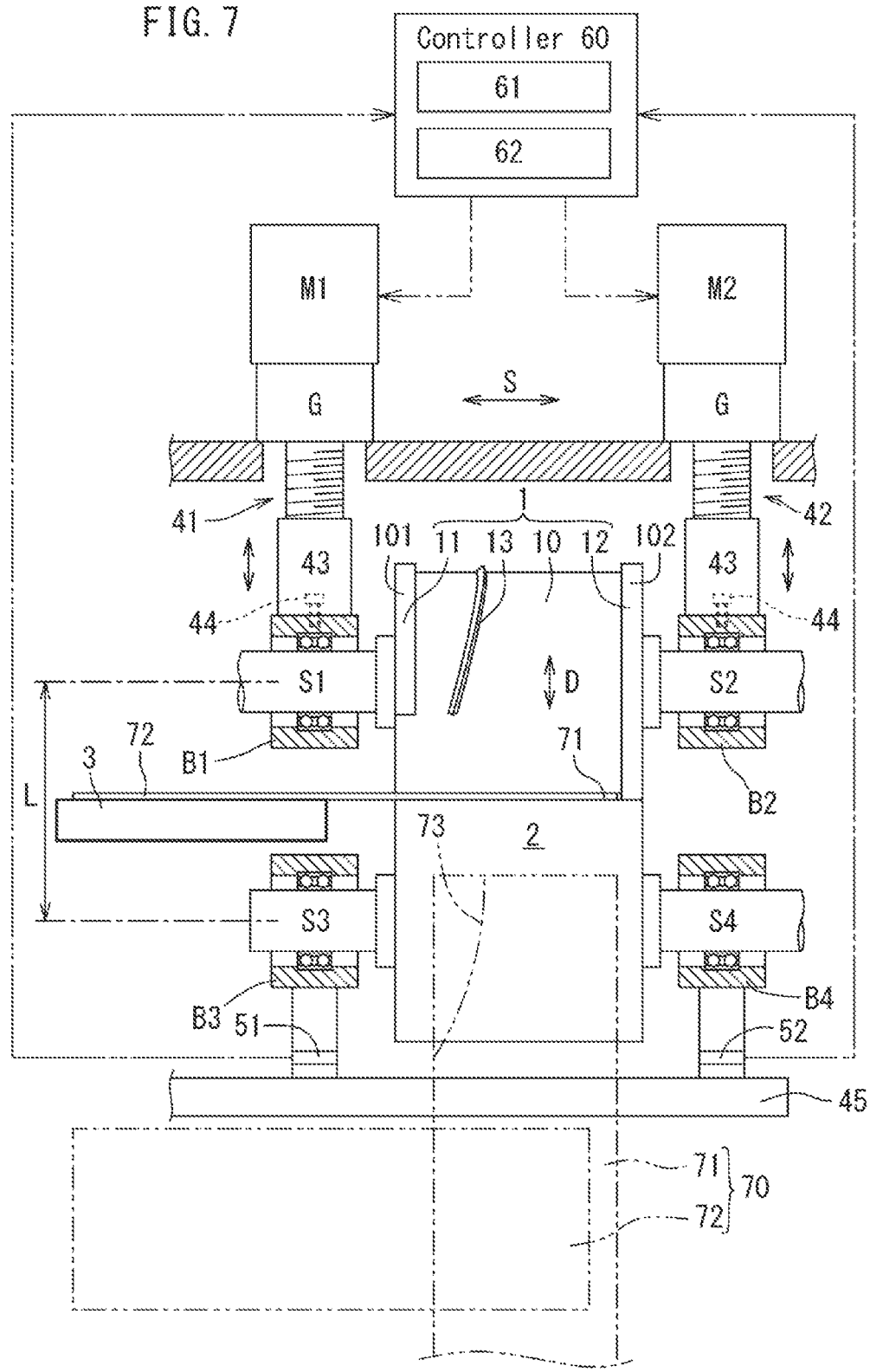

PROCESSING DEVICE FOR ABSORBENT ARTICLE

TECHNICAL FIELD

The present invention relates to an absorbent article processing device.

BACKGROUND ART

As the processing, conventionally, a part of a laminate is cut by a cutter roll that is in contact with an anvil roll (the first patent document).

In this prior art technology, a blade is provided on an outer circumference of a roll main body of the cutter roll, and a pair of bearers being in contact with the anvil roll are provided around the entire circumference of both ends of the roll main body.

CITATION LIST

Patent Literature

[The first patent document] JP2007-229898 A2 (front page)

SUMMARY OF INVENTION

In the prior art technology, a workpiece passes between a pair of bearers. Accordingly, when the workpiece is long in an axial direction of the cutter roll, it is inevitable that the cutter roll and the anvil roll become long in the axial direction.

Increase in the length of each of the cutter roll and the anvil roll in this way may increase not only the size of a processing device, but also a bending moment due to a load applied to the roll, resulting in easily causing distortion in each roll to deteriorate a cutting function.

Therefore, an object of the present invention is to provide an absorbent article processing device which can be reduced in size and in which a cutting function is not easily deteriorated.

An absorbent article processing device of the present invention is a processing device for an absorbent article 7, the processing device including a cutter roll 1 and an anvil roll 2 with which the cutter roll 1 is brought into contact, the cutter roll 1 including:

a roll main body 10;

a blade 13 provided on an outer circumferential surface 10s of the roll main body 10 and protruding in a radial direction D of the roll main body 10 in a first angular range α of a part of a circumferential direction R of the roll main body 10;

a first bearer 11 protruding in the radial direction D of the roll main body 10 and being in contact with the anvil roll 2 in a second angular range β of a part of the circumferential direction R including at least the first angular range α at a first end portion 101 in an axial direction S of the roll main body 10, and the first bearer 11 being cut out in an angular range γ in an entire circumference excluding the second angular range β at the first end portion 101; and a second bearer 12 provided around the entire circumference or a part of the circumferential direction at a second end portion 102 in the axial direction S of the roll main body 10, and the second bearer 12 being in contact with the anvil roll 2.

In the present invention, the blade 13 is brought into contact with an outer circumferential surface of the anvil roll 2 via the absorbent article 7, thus cutting a part of the absorbent article 7. During the cutting, in the second angular range β that is not smaller than the first angular range α provided with the blade 13, both the first bearer 11 and the second bearer 12 are brought into contact with the anvil roll 2. Consequently, the blade 13 can cut a part of the absorbent article 7 with an appropriate contact pressure. Furthermore, damage of the blade 13 can be suppressed.

On the other hand, the first bearer 11 is cut out in a remaining angular range γ excluding the second angular range β. Consequently, during non-cutting, a workpiece can pass between the first end portion 101 and the anvil roll 2. Therefore, when the workpiece intermittently includes absorbent main bodies 72, both rolls can be shortened in the axial direction.

In this way, each roll can be shortened, so that a processing device can be reduced in size. In addition, a bending moment due to a load applied to the roll is reduced, and distortion of each roll is reduced. Thus, the cutting function is maintained.

In the present invention, "including at least a first angular range α" may include a case where the first angular range α is encompassed in the second angular range β, and a case where the first angular range α and the second angular range β are the same angular range (in a range in which the first angular range α and the second angular range β completely overlap each other in the circumferential direction).

In the present invention, the first bearer 11 may extend completely continuously in the circumferential direction R in the second angular range β, or may be partially discontinuously (for example, partially intermittent with a cutout, or the like). At the first end portion 101, a range from an upstream-side end to a downstream-side end in the rotation direction provided with the first bearer 11 is the second angular range β, and a remaining range not provided with the first bearer 11 is an angular range γ.

BRIEF DESCRIPTION OF EMBODIMENTS

Figure 5A:
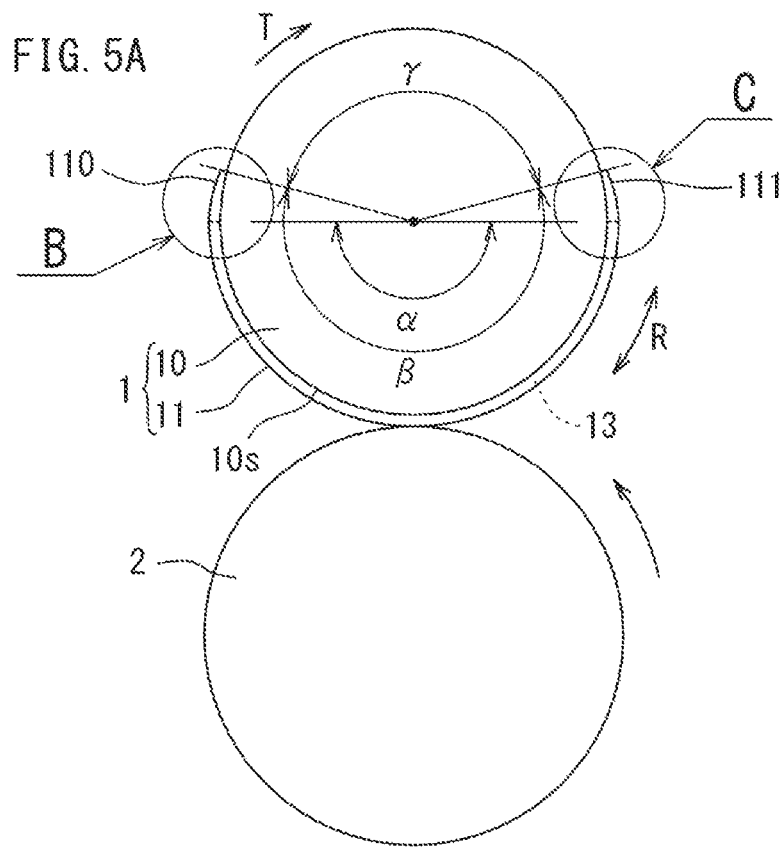
Figure 5B:
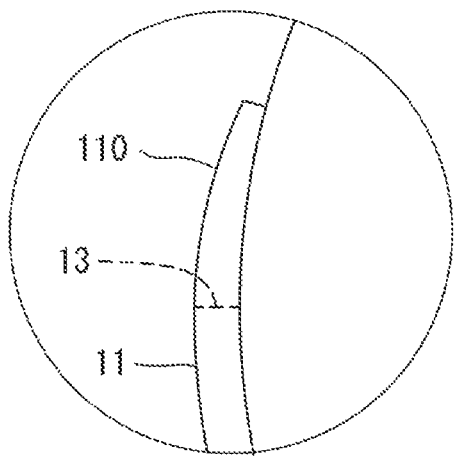
Figure 5C:
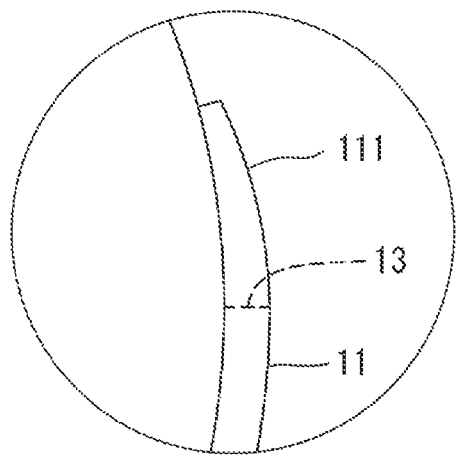

FIG. 5A is a conceptual side view showing a first bearer; FIG. 5B is an enlarged view of an upstream-side end portion in the rotation direction of the first bearer; FIG. 5C is an enlarged view of a downstream-side end portion in the rotation direction of the first bearer.

Figure 6:
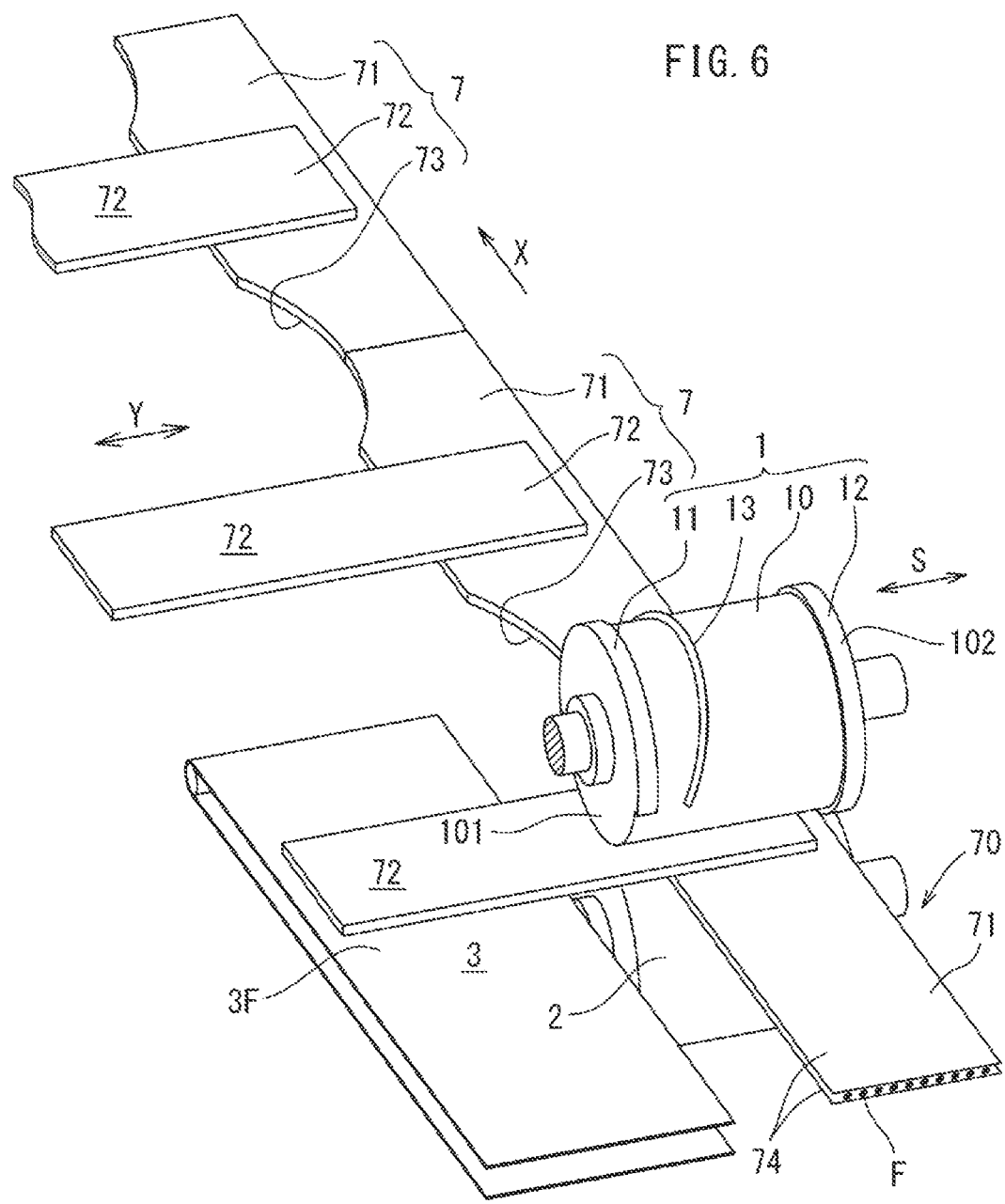

FIG. 6 is a schematic perspective view showing an example of a processing device during non-cutting.

FIG. 7 is a schematic configuration view of the processing device during non-cutting.

BRIEF DESCRIPTION OF EMBODIMENTS

Preferably, the second angular range β is larger than the first angular range α;

an upstream-side end portion 110, in a rotation direction T, of the first bearer 11 extends in the circumferential direction R of the first bearer 11 more than one end of the blade 13, the one being at an upstream side in the rotation direction T; and a downstream-side end portion ill, in the rotation direction T, of the first bearer 11 extends in the circumferential direction R more than another end of the blade 13, the other end being at a downstream side in the rotation direction T of the blade 13.

In this case, the first bearer 11 extending in the circumferential direction R more than the both ends of the blade 13 will suppress damage of the blade 13.

Further preferably, at least in the upstream-side end portion 110 in the rotation direction T of the first bearer 11, the first bearer 11 extending in the circumferential direction R is formed in such a manner that a protrusion amount protruding in the radial direction D is gradually reduced toward a tip end of the upstream-side end portion 110.

In this case, the tapering end portion 110 of the first bearer 11 starts to come in contact with an outer circumferential surface of the anvil roll 2 from the tip end, and a contact pressure between the first bearer 11 and the anvil roll 2 will be gradually increased by the time when the blade 13 is brought into contact with the anvil roll 2. Consequently, a rapid increase in the contact pressure between the first bearer 11 and the anvil roll 2 will be relieved, and vibration by the contact will be suppressed. Furthermore, the cutter roll 1 will rotate smoothly, so that trimming will be performed by the blade 13 more smoothly.

The processing device preferably includes:

a first bearing B1 and a second bearing B2 of the cutter roll 1, the first bearing B1 and the second bearing B2 axially supporting a first shaft S1 and a second shaft S2, respectively, and the first shaft S and the second shaft S2 protruding from a first end portion 101 and a second end portion 102 of the roll main body 10, respectively;

a first bearing B3 and a second bearing B4 of the anvil roll 2, the first bearing B3 and the second bearing B4 axially supporting a first shaft S3 and a second shaft S4 of the anvil roll 2, respectively; and a carrying device 3 placed between the first bearing B1 of the cutter roll 1 and the first bearing B3 of the anvil roll 2, and carrying a part of the absorbent article 7.

Carrying device 3 is placed between the first bearing B1 of the cutter roll 1 and the first bearing B3 of the anvil roll 2, and the carrying device 3 carries a site (an absorbent main body) as a part of the absorbent article 7. Thus, the lengths of the axial direction S of roll main body portions of the cutter roll 1 and the anvil roll 2 can be shortened.

Therefore, the sizes of the cutter roll 1 and the anvil roll 2 can be reduced.

In particular, since the cutter roll 1 and the anvil roll 2 are shortened, the bending moment generated in the rolls is reduced to reduce distortion of the both rolls. Consequently, the cutting function is not easily deteriorated.

Further preferably, in the processing device, wherein the absorbent article 7 is processed from a continuous laminate 70 intermittently having absorbent main bodies 72 in a carrying direction X, each of the absorbent main bodies 72 protruding in a direction Y perpendicular to the carrying direction X from an around-torso member 71 continuous in the carrying direction X, and the carrying device 3 is a carrying conveyor for carrying the absorbent main bodies 72 of the continuous laminate 70 in the carrying direction X.

The around-torso member 71 of the absorbent article 7 is generally formed of a thin material, and accordingly the sharpness may often be dull. On the contrary, as described above, the cutting function of the blade 13 is not easily deteriorated, and consequently, even a thin material can be cut smoothly and stably.

For example, the blade 13 may trim a part of the around-torso member 71 of the continuous laminate 70 to form a notch as a leg hole 73 of the absorbent article 7.

Preferably, the processing device includes a first bearing B1 and a second bearing B2 of the cutter roll 1, the first bearing B1 and the second bearing B2 axially supporting a first shaft S1 and a second shaft S2, respectively, and the first shaft S and the second shaft S2 protruding from a first end portion 101 and a second end portion 102 of the roll main body 10, respectively;

a first bearing B3 and a second bearing B4 of the anvil roll 2, the first bearing B3 and the second bearing B4 axially supporting a first shaft S3 and a second shaft S4 of the anvil roll 2, respectively;

a first pressing mechanism 41 for pressing the first bearing B1 of the cutter roll 1 toward the first bearing B3 of the anvil roll 2 in the radial direction;

a first detector 51 for detecting a load in the radial direction on the first bearing B3 of the anvil roll 2; and a first control unit 61 for controlling a physical quantity corresponding to an axial distance L between the cutter roll 1 and the anvil roll 2 by controlling the first pressing mechanism 41 in response to an output from the first detector 51.

In this case, the first pressing mechanism 41 is controlled in response to a load detected by the first detector 51. Even if the first bearer 11 is partially cut out, the axial distance L can be controlled in a predetermined range. Consequently, the cutting function will be stable.

The "physical quantity corresponding to an axial distance L" may control the axial distance L itself, but may control the position of the shaft S1 of the cutter roll 1, or may control a rotation angle of the servo motor as mentioned below.

Further preferably, the processing device includes a second pressing mechanism 42 for pressing the second bearing B2 of the cutter roll 1 toward the second bearing B4 of the anvil roll 2 in the radial direction;

a second detector 52 for detecting a load in the radial direction on the second bearing B4 of the anvil roll 2; and a second control unit 62 for controlling the second pressing mechanism 42 in response to an output from the second detector 52.

In this case, the second pressing mechanism 42 is controlled in response to the load detected by the second detector 52, so that a contact pressure at a second end portion 102 side of the cutter roll 1 with respect to the anvil roll 2 will be stable. Consequently, even if the first bearer 11 is partially cut out, a contact state of the second bearer 12 will be stable.

Further preferably, the first pressing mechanism 41 and the second pressing mechanism 42 comprise a first servo motor M1 and a second servo motor M2, respectively, the first pressing mechanism 41 comprises a conversion mechanism 43 for converting a rotation force of the first servo motor M1 into an axial force in the radial direction, and the second pressing mechanism 42 comprises a conversion mechanism 43 for converting a rotation force of the second servo motor M2 into an axial force in the radial direction.

In this case, the axial distance L and the load will be controlled easily.

Further preferably, the first control unit 61 controls the first pressing mechanism 41 such that the axial distance L between the cutter roll 1 and the anvil roll 2 is in a predetermined range.

In this case, the cutter roll 1 will rotate smoothly, and a cutting function of the blade 13 will be stable.

Further preferably, the second control unit 62 controls the second pressing mechanism 42 such that a rotation torque of the second servo motor M2 is in a predetermined range.

In this case, a contact pressure between the blade 13 and the anvil roll 2 will be stable, and the cutting function of the blade 13 will be stable.

Preferably, the first pressing mechanism 41 is fixed to an outer cylindrical portion of the first bearing B1 of the cutter roll 1, the second pressing mechanism 42 is fixed to an outer cylindrical portion of the second bearing B2 of the cutter roll 1, and the first servo motor M1 and the second servo motor M2 are rotated in synchronization with each other so as to enable the cutter roll 1 to be separated from the anvil roll 2.

In this case, the cutter roll 1 can be separated from the anvil roll 2, and the cutter roll 1 can be subjected to checking, maintenance, or replacement. A manual operation of allowing a web to pass between the cutter roll 1 and the anvil roll 2 can be facilitated.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Prior to description of an example of the processing device of the present invention, an example of an absorbent article (disposable worn article) 7 as a workpiece, and an outline of processing procedure will be described.

Figure 1:
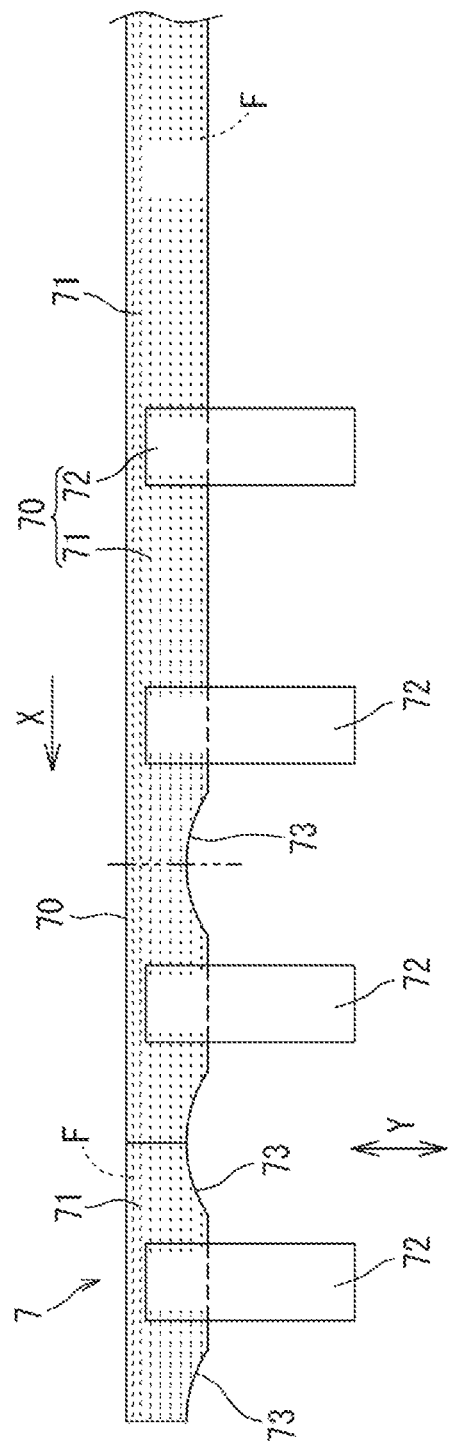
FIG. 1 is a plan view showing an example of a method for processing an absorbent article according to the present invention.

As shown in the left end of FIG. 1, the absorbent article 7 is, for example, a T-type disposable diaper. The diaper includes an around-torso member 71, and an absorbent main body 72 protruding in a longitudinal direction Y perpendicular to an around-torso direction of the around-torso member 71.

The absorbent main body 72 of FIG. 1 is provided with an absorbing core not shown. The absorbing core absorbs a body fluid. The absorbing core is sandwiched between a top sheet and a back sheet. The top sheet, the absorbing core, and the back sheet are laminated onto each other.

The top sheet is made of a thin liquid-permeable non-woven fabric, and covers a skin surface of the absorbing core. On the top sheet, a cuff not shown may be provided.

The back sheet covers non-skin surface of the absorbing core, and is made of non-liquid-permeable resin sheet. The around-torso member 71 is attached to one end portion in the longitudinal direction Y of the absorbent main body 72. The around-torso member 71 protrudes from the absorbent main body 72 in the around-torso direction.

The around-torso member 71 is provided with an elastic member F for fitting the absorbent article 7 to a wearer. The elastic member F may be, for example, a plurality of rubber threads, rubber tapes (thermoplastic elastomer), or a material including a thermoplastic resin, or the like. Furthermore, the elastic member F may be nullified (made into a state in which a shrinkage force is not exerted) in a portion layered onto the absorbent main body 72. Each elastic member F may extend in parallel in the around-torso direction.

The around-torso member 71 has notches serving as leg holes 73. The notches are provided to both sides of the absorbent main body 72 by trimming processing mentioned below.

Next, an outline of a processing step of the absorbent article 7 will be described.

Figure 2:
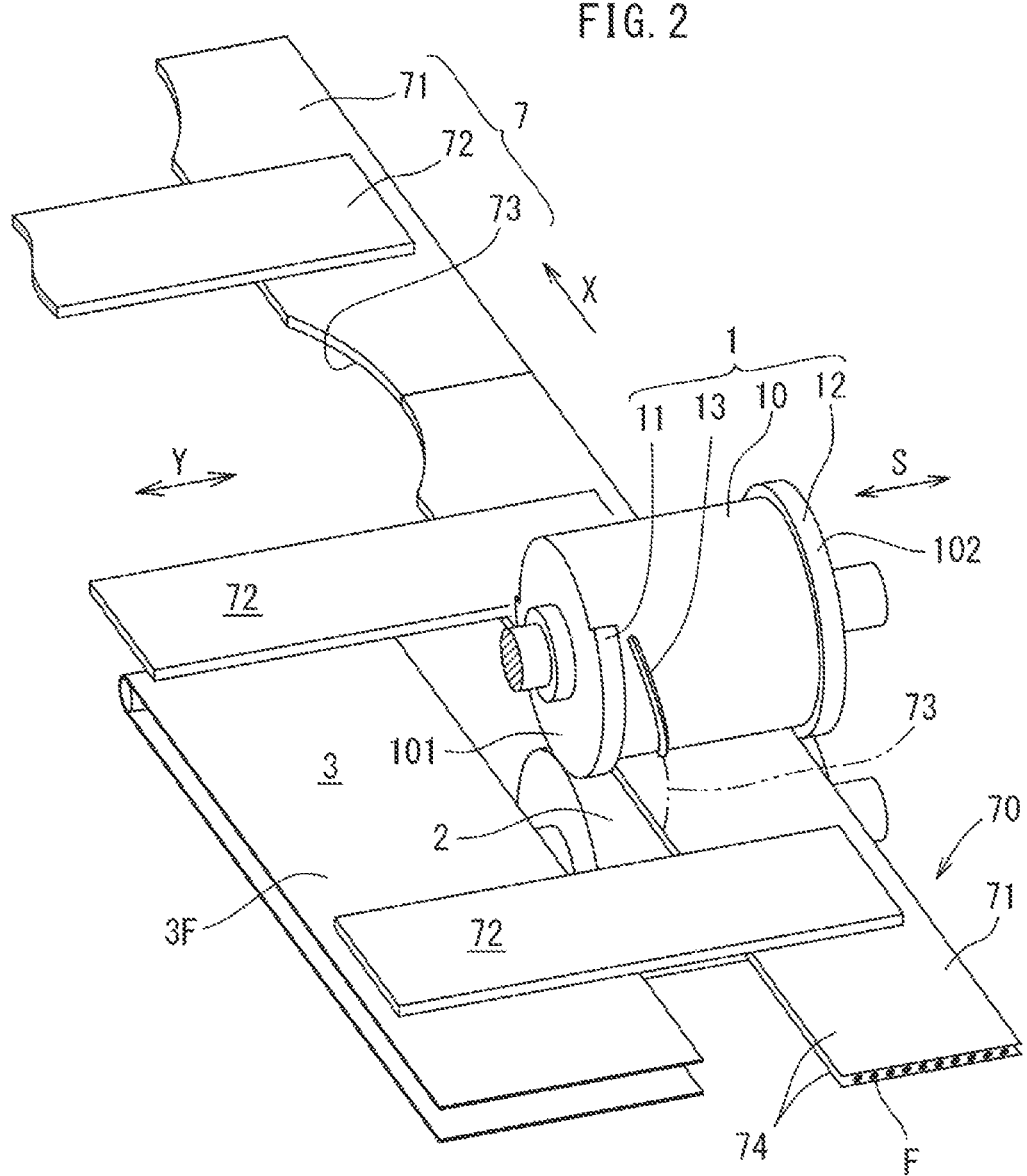
FIG. 2 is a schematic perspective view showing an example of a processing device during cutting in the present invention.

In FIGS. 1 and 2, a plurality of continuous elastic members F extending in the carrying direction X is carried in the carrying direction X in a state where elastic members F are stretched in the carrying direction X. On the other hand, the continuous elastic members F are sandwiched between two continuous first and second non-woven fabrics 74, 74 (FIG. 2), and the first and second continuous non-woven fabrics 74, 74 are bonded to each other with an adhesive agent such that they are layered to each other. Thus, the around-torso member 71 is formed.

Note here that the bonding may be heat-sealing (thermal welding), or may be welding by ultrasonic energy.

The elastic members F in the around-torso member 71 of FIG. 1 are cut and nullified in a portion layered onto the absorbent main body 72.

Thereafter, the absorbent main bodies 72 are intermittently placed in the around-torso member 71. That is, the absorbent main bodies 72 are intermittently placed in the carrying direction X in such a manner that each absorbent main body 72 protrudes in the direction Y perpendicular to the carrying direction X from the around-torso member 71 continuous in the carrying direction X. Thus, a continuous laminate 70 is formed.

By the below-mentioned processing device, in the continuous laminate 70, a part of the around-torso member 71 is trimmed to form notches as the leg holes 73 of the absorbent article 7.

Thereafter, the continuous laminate 70 of FIG. 1 is cut along a virtual cutting line shown by a two-dot chain line into a size (unit) of each individual worn article (absorbent article) 7. That is, in order to form individual worn articles 7 one after another, the continuous laminates 70 are cut one after another in the longitudinal direction Y between the absorbent main bodies 72 neighboring in the carrying direction X.

Note here that the absorbent main bodies 72 and the leg holes 73 are folded at any appropriate times.

Next, an example of the processing device will be described.

In FIG. 2, the processing device includes a cutter roll 1, an anvil roll 2 with which the cutter roll 1 is brought into contact, and a carrying device 3. The carrying device 3 is a carrying conveyor for carrying the absorbent main body 72 of the continuous laminate 70 in the carrying direction X.

Note here that the around-torso member 71 of the continuous laminate 70 is carried to be wound to a plurality of other rolls (not shown) while being sandwiched between a pair of rolls 1 and 2.

The cutter roll 1 includes a roll main body 10, a first bearer 11, a second bearer 12, and a blade 13.

The blade 13 is brought into contact with an outer circumferential surface (cylindrical surface) of the anvil roll 2 via the around-torso member 71 and trims (die-cuts) a part of the around-torso member 71 to form leg holes 73 in the around-torso member 71.

As shown in FIGS. 5A to 5C, the blade 13 protrudes only in the first angular range α that corresponds to a part of the roll main body 10 along the circumferential direction R.

The second bearer 12 in FIGS. 2 and 6 is provided around the entire circumference at the second end portion 102, in the axial direction S, of the roll main body 10. The second bearer 12 is brought into contact with the outer circumferential surface of the anvil roll 2 both during processing in FIG. 2 and during non-processing in FIG. 6.

On the other hand, the first bearer 11 is provided to the first end portion 101, in the axial direction S, of the roll main body 10. The first bearer 11 is partially cut out (i.e., not provided) in the circumferential direction R. Therefore, the first bearer 11 is not in contact with the anvil roll 2 during non-processing in FIG. 6, and is brought into contact with the anvil roll 2 during processing in FIG. 2.

As shown in FIGS. 7 and 6, the around-torso member 71 of the continuous laminate 70 and a part of the absorbent main body 72 pass through between the roll main body 10 and the anvil roll 2 as well as between the first bearer 11 and the second bearer 12.

That is, as shown in FIGS. 2 to 3, and 5A to 5C, the first bearer 11 protrudes in the radial direction of the roll main body 10 and is brought into contact with the anvil roll 2 in the second angular range β. The first bearer 11 is cut out in the remaining angular range γ, in which the second angular range β is excluded from an entire circumference. The second angular range β is a part of the circumferential direction R, and includes at least the first angular range α.

In FIG. 5A, the second angular range β is larger than the first angular range α. Both end portions 110 and 111 in the circumferential direction R of the first bearer 11 protrude (extend) toward the circumferential direction R from both ends in the circumferential direction R of the blade 13. In other words, a tip end of the end portion 110 of the first bearer 11 is positioned at a more upstream side in the rotation direction than the upstream side, in the rotation direction, of the blade 13, and a tip end of the end portion 111 of the first bearer 11 is positioned at a more downstream side in the rotation direction than an end of the blade 13, which is at the downstream side in the rotation direction.

As shown in FIG. 5B, in the upstream-side end portion 110 in the rotation direction T of the first bearer 11, the first bearer 11 protruding toward the circumferential direction R may be reduced in the protrusion amount protruding in a tapering manner in the radial direction toward the tip end at the upstream side in the rotation direction T. That is, the end portion 110 may be gradually reduced in the protrusion amount as the end portion 110 extends toward the tip end at the upstream side.

Furthermore, as shown in FIG. 5C, in the downstream-side end portion 111 in the rotation direction T of the first bearer 11, the first bearer 11 protruding toward the circumferential direction R may be reduced in the a protrusion amount protruding in a tapering manner in the radial direction toward the tip end in the downstream side in the rotation direction T. That is, the end portion 111 may be gradually reduced in the protrusion amount as the end portion 111 extends toward the tip end at the downstream side.

Figure 3:
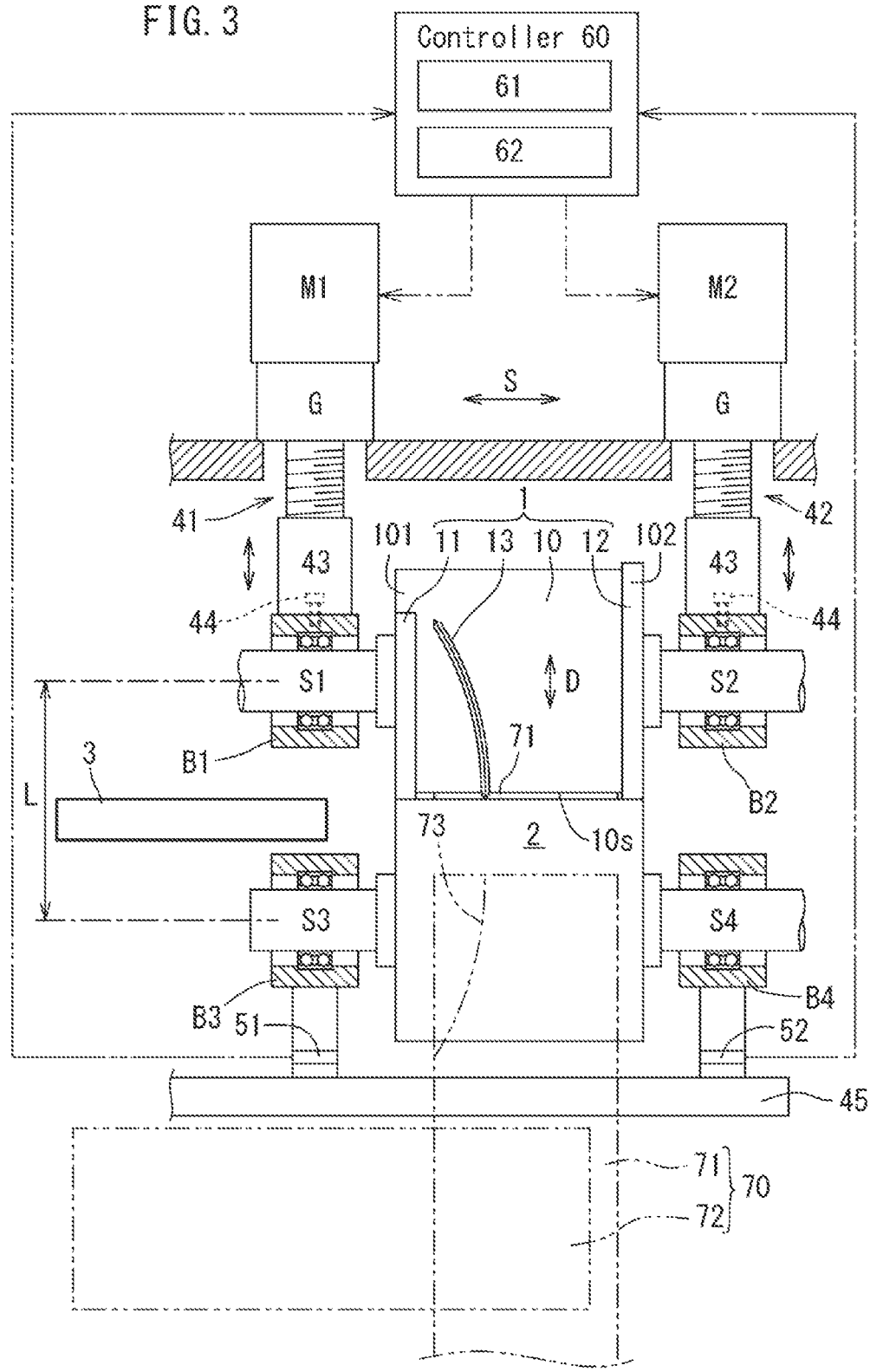
FIG. 3 is a schematic configuration view of the processing device during cutting.

As shown in FIGS. 3 and 7, the cutter roll 1 and the anvil roll 2 are provided with the first and second bearings B1 to B4.

The first bearing B1 and the second bearing B2 of the cutter roll 1 axially support the first shaft S1 and the second shaft S2, respectively. The first shaft S1 and the second shaft S2 protrude from the first end portion 101 and second end portion 102 of the roll main body 10, respectively.

The first bearing B3 and the second bearing B4 of the anvil roll 2 axially support the first shaft S3 and the second shaft S4 of the anvil roll 2, respectively.

Figure 4:
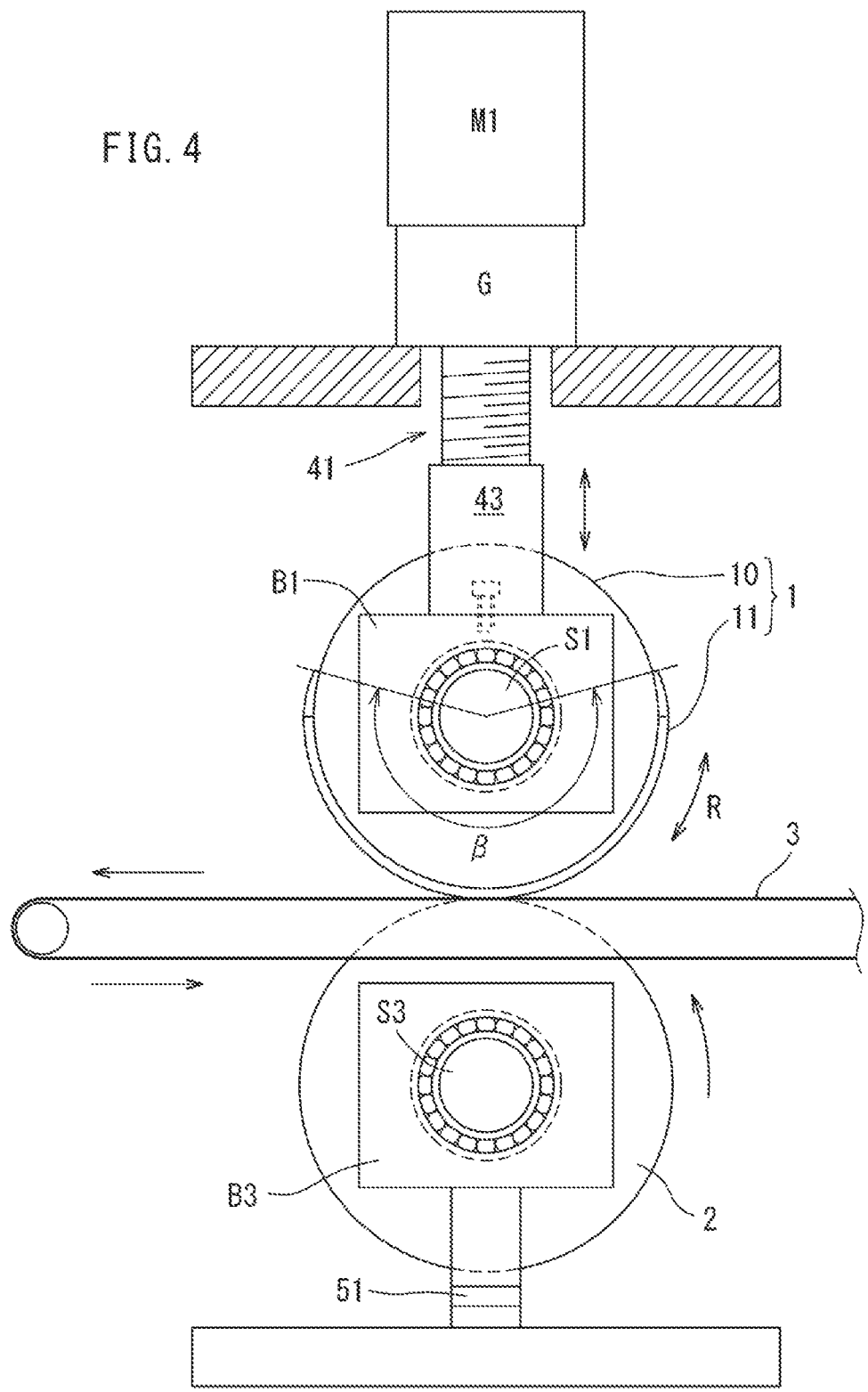
FIG. 4 is a schematic side view of the processing device during cutting.

The carrying device 3 is placed between the first bearing B1 of the cutter roll 1 and the first bearing B3 of the anvil roll 2, and carries the absorbent main bodies 72 of the absorbent article 7. As shown in FIGS. 4 and 2, the carrying surface 3F of the carrying device 3 may extend along the plane on which the cutter roll 1 and the anvil roll 2 are brought into contact with each other, and along the carrying direction X of the around-torso member 71.

In FIG. 3, the first bearing B1 and the second bearing B2 of the cutter roll 1 are respectively linked to the first pressing mechanism 41 and the second mechanism 42 by binding tools such as a bolt 44 shown by a broken line. On the other hand, each of the first bearing S3 and the second bearing S4 of the anvil roll 2 is supported by a frame 45.

This processing device includes a pair of pressing mechanisms 41 and 42, a pair of detectors 51 and 52, and a pair of control units 61 and 62. The first and second control units 61 and 62 may be separate programs incorporated in one controller 60.

In FIG. 3, the first pressing mechanism 41 and the second pressing mechanism 42 respectively include the servo motor M1 and the servo motor M2. The first pressing mechanism 41 includes the conversion mechanism 43 for converting the rotating force of the servo motor M1 into a pressing axial force acting in the radial direction. The second pressing mechanism 42 includes the conversion mechanism 43 for converting the rotation force of the servo motor M2 into a pressing axial force acting in the radial direction. As the conversion mechanism 43, for example, a ball screw may be employed. Furthermore, a reduction gear G for increasing a rotation torque of the servo motor may be linked to the output axis of the servo motor.

In FIG. 3, a rotation torque of the first servo motor M1 and a rotation torque of the second and M2 are increased via the reduction gear G, and converted into the axial force via the conversion mechanism 43. The axial force generated in the first pressing mechanism 41 is a load compressing the first detector 51 via the first bearing B, the first shaft S1, the cutter roll 1, the anvil the roll 2, the first shaft S3 and the first bearing B3.

On the other hand, the axial force generated in the second pressing mechanism 42 becomes a load compressing the second detector 52 via the second bearing B2, the second shaft S2, the cutter roll 1, the anvil roll 2, the second shaft S4, and the second bearing B4.

In FIG. 3, the first pressing mechanism 41 and the second pressing mechanism 42 are respectively fixed to the outer cylindrical portion of the first bearing B1 and the outer cylindrical portion of the second bearing B2. The first servo motor M1 and the second servo motor M2 rotate in synchronization with each other, thus enabling the cutter roll 1 to be separated from the anvil roll 2.

The first pressing mechanism 41 presses the first bearing B1 of the cutter roll 1 in the radial direction toward the first bearing B3 of the anvil roll 2. The first detector 51 detects a load in the radial direction on the first bearing B3 of the anvil roll 2.

The first control unit 61 controls the first pressing mechanism 41 in response to an output from the first detector 51 so as to control the physical quantity corresponding to the axial distance L between the roll 1 and the roll 2. As the physical quantity, for example, an axial distance L itself may be controlled, or a rotation angle or a torque of the first servo motor M1 may be controlled.

In FIG. 3, the second pressing mechanism 42 presses the second bearing B2 of the cutter roll 1 toward the second bearing B4 of the anvil roll 2 in the radial direction. The second detector 52 detects a load in the radial direction on the second bearing B4 of the anvil roll 2. The second control unit 62 controls the second pressing mechanism 42 in response to an output from the second detector 52.

In FIG. 3, the first control unit 61 may control the first pressing mechanism 41 such that the axial distance L between the roll 1 and the roll 2 is within a predetermined range. Furthermore, the second control unit 62 may control the second pressing mechanism 42 such that the rotation torque of the second servo motor M2 is within a predetermined range.

Next, a trimming step will be described.

As shown in FIG. 2, when only a portion of the around-torso member 71 of continuous laminate 70 is supplied between the cutter roll 1 and the anvil roll 2, the around-torso member 71 is cut by the blade 13 as shown in a two-dot chain line. At this time, the absorbent main body 72 of the continuous laminate 70 is carried by the carrying device 3 in the carrying direction X.

As shown in FIGS. 7 and 6, at the time of non-processing (during non-processing) after trimming by the cutting, the non-processed portion of the cutter roll 1 (corresponding to an angular range γ of FIG. 5A) which is not provided with the first bearer 11 and the blade 13 faces the anvil roll 2. As shown in FIGS. 7 and 6, the absorbent main body 72 passes through a gap between the non-processing portion of the cutter roll 1 and the anvil roll 2. That is, during the non-processing, the continuous laminate 70 passes through the gap between the cutter roll 1 and the anvil roll 2 without being trimmed.

Next, a method for controlling the axial distance L of FIG. 3 will be described.

In FIG. 3, during operation, the second bearer 12 is always in contact with the anvil roll 2. On the other hand, the first bearer 11 is in contact with the anvil roll 2 during processing, but is not in contact with the anvil roll 2 during non-processing. Accordingly, it is desired that the axial distance L is kept in a predetermined range value, and a contact pressure between the blade 13 and the anvil roll 2 or rotation of the cutter roll 1 are stabilized.

Now, when the load detected by the first detector 51 is too large with respect to a first set value, the axial distance L will be too small. Thus, the first control unit 61 controls the rotation angle of the servo motor M1 such that the axial distance L is increased.

On the other hand, when the load detected by the first detector 51 is too small with respect to the first set value, the axial distance L will be too large. Thus, the first control unit 61 controls the rotation angle of the servo motor M1 such that the axial distance L is reduced.

Furthermore, when the load detected by the second detector 52 is too large with respect to a second set value, the contact pressure will be too large. Thus, the second control unit 62 controls the rotation angle of the servo motor M2 such that the load detected by second detector 52 is reduced.

Furthermore, when the load detected by the second detector 52 is too small with respect to the second set value, the contact pressure will be too small. Thus, the second control unit 62 controls the rotation angle of the servo motor M2 such that the load detected by second detector 52 is increased.

Thus, control is performed such that the axial distance L of FIG. 3 is in a predetermined range. Furthermore, control is performed such that the contact pressure between the blade 13 and the anvil roll 2 of the cutter roll 1 becomes a predetermined value.

By the way, in a case where the cutter roll 1 is subjected to checking, maintenance, or replacement, or in a case where the continuous laminate 70 to be processed is changed, the servo motors M1 and M2 are rotated in synchronization with each other to separate the cutter roll 1 from the anvil roll 2.

Next, a shape or the like of the second bearer 12 will be briefly described.

The second bearer 12 of FIG. 2 is provided around the entire circumference or a part of the circumferential direction at the second end portion of the roll main body. Herein, the second bearer 12 may have the same shape and dimension as those of the first bearer 11, and may be provided in the same position in the circumferential direction.

That is, in the second end portion 102 in the axial direction S of the roll main body 10, similar to the first bearer 11 of FIG. 5A, the second bearer 12 may protrude in the radial direction D of the roll main body 10 (FIG. 3) and be brought into contact with the anvil roll 2 in the second angular range β of a part in the circumferential direction R including at least the first angular range α, and may be cut out (i.e., not provided) in the angular range γ excluding the second angular range β.

Furthermore, similar to the first bearer 11 of FIGS. 5B and 5C, both end portions in the circumferential direction R of the second bearer 12 may protrude in the circumferential direction R from both ends of the circumferential direction R of the blade 13.

Similarly, at least in the upstream-side end portion in the rotation direction of the second bearer 12, the second bearer 12 protruding in the circumferential direction R may be reduced in the protrusion amount protruding in the radial direction D in a manner of tapering toward the tip end of the second bearer 12 at the upstream side.

Preferred embodiments have been described above with reference to the drawings, but obvious variations and modifications will readily occur to those skilled in the art upon reading the present specification.

For example, the worn articles may be not only a T-type but also an H-type.

Furthermore, a site to be cut may not be an around-torso member, but may be an absorbent main body.

Therefore, such changes and modifications are deemed to fall within the scope of the present invention, which is defined by the appended claims.

INDUSTRIAL APPLICABILITY

The present invention is applicable to worn articles such as disposable diapers and disposable pants, as well as absorbent articles such as sanitary products.

REFERENCE SIGNS LIST

1: Cutter roll, 10: Roll main body, 10s: Outer circumferential surface, 11: First bearer, 110: Upstream-side end portion, 111: Downstream-side end portion, 12: Second bearer, 13: Blade,
101: First end portion, 102: Second end portion,
2: Anvil roll, 3: Carrying device, 3F: Carrying surface,
41: First pressing mechanism, 42: Second pressing mechanism, 43: Conversion mechanism
44: Bolt, 45: Frame
51: First detector, 52: Second detector,
60: Controller, 61: First control unit, 62: Second control unit,
7: Absorbent article, 70: Continuous laminate, 71: Around-torso member,
72: Absorbent main body,
73: Leg hole, 74: Continuous non-woven fabric
α, β, γ: Angular range
G: Reduction gear
M1, M2: Servo motor
R: Circumferential direction, S: Axial direction, T: Rotation direction,
S1 to S4: Shaft
B1 to B4: Bearing
X: Carrying direction, Y: Perpendicular direction

The invention claimed is:

1. A processing device for an absorbent article, the processing device including a cutter roll and an anvil roll with which the cutter roll is brought into contact, the cutter roll comprising:
   a roll main body;
   a blade provided on an outer circumferential surface of the roll main body and protruding in a radial direction of the roll main body in a first angular range of a part of a circumferential direction of the roll main body;
   a first bearer protruding in the radial direction of the roll main body and being in contact with the anvil roll in a second angular range of a part of the circumferential direction including at least the first angular range at a first end portion in an axial direction of the roll main body, and the first bearer being cut out in an angular range in an entire circumference excluding the second angular range at the first end portion; and
   a second bearer provided around the entire circumference or a part of the circumferential direction at a second end portion in the axial direction of the roll main body, and the second bearer being in contact with the anvil roll.

2. The processing device according to claim 1, wherein the second angular range is larger than the first angular range;
   an upstream-side end portion, in a rotation direction, of the first bearer extends in the circumferential direction of the first bearer more than one end of the blade, the one end being at an upstream side in the rotation direction; and
   a downstream-side end portion, in the rotation direction, of the first bearer extends in the circumferential direction more than another end of the blade, the other end being at a downstream side in the rotation direction of the blade.

3. The processing device according to claim 2, wherein at least in the upstream-side end portion in the rotation direction of the first bearer, the first bearer extending in the circumferential direction is formed in such a manner that a protrusion amount protruding in the radial direction is gradually reduced toward a tip end of the upstream-side end portion.

4. The processing device according to claim 1, comprising:
   a first bearing and a second bearing of the cutter roll, the first bearing and the second bearing axially supporting a first shaft and a second shaft, respectively, and the first shaft and the second shaft protruding from the first end portion and the second end portion of the roll main body, respectively;
   a first bearing and a second bearing of the anvil roll, the first bearing and the second bearing axially supporting a first shaft and a second shaft of the anvil roll respectively; and
   a carrying device placed between the first bearing of the cutter roll and the first bearing of the anvil roll, and carrying a part of the absorbent article.

5. The processing device according to claim 4, wherein the absorbent article is processed from a continuous laminate intermittently having absorbent main bodies in a carrying direction, each of the absorbent main bodies protruding in a direction perpendicular to the carrying direction from an around-torso member continuous in the carrying direction, and
   the carrying device is a carrying conveyor for carrying the absorbent main bodies of the continuous laminate in the carrying direction.

6. The processing device according to claim 5, wherein the blade trims a part of the around-torso member of the continuous laminate to form a notch as a leg hole of the absorbent article.

7. The processing device according to claim 1, comprising:
   a first bearing and a second bearing of the cutter roll, the first bearing and the second bearing axially supporting a first shaft and a second shaft, respectively, and the first shaft and the second shaft protruding from the first end portion and the second end portion of the roll main body, respectively;
   a first bearing and a second bearing of the anvil roll, the first bearing and the second bearing axially supporting a first shaft and a second shaft of the anvil roll, respectively;
   a first pressing mechanism for pressing the first bearing of the cutter roll toward the first bearing of the anvil roll in the radial direction;
   a first detector for detecting a load in the radial direction on the first bearing of the anvil roll; and
   a first control unit for controlling a physical quantity corresponding to an axial distance between the cutter roll and the anvil roll by controlling the first pressing mechanism in response to an output from the first detector.

8. The processing device according to claim 7, comprising:
   a second pressing mechanism for pressing the second bearing of the cutter roll toward the second bearing of the anvil roll in the radial direction;
   a second detector for detecting a load in the radial direction on the second bearing of the anvil roll; and
   a second control unit controlling the second pressing mechanism in response to an output from the second detector.

9. The processing device according to claim 8, wherein the first pressing mechanism and the second pressing mechanism comprise a first servo motor and a second servo motor, respectively,
   the first pressing mechanism comprises a conversion mechanism for converting a rotation force of the first servo motor into an axial force in the radial direction, and the second pressing mechanism comprises a conversion mechanism for converting a rotation force of the second servo motor into an axial force in the radial direction.

10. The processing device according to claim 9, wherein the first control unit controls the first pressing mechanism such that the axial distance between the cutter roll and the anvil roll is in a predetermined range.

11. The processing device according to claim 10, wherein the second control unit controls the second pressing mechanism such that a rotation torque of the second servo motor is in a predetermined range.

12. The processing device according to claim 9, wherein the first pressing mechanism is fixed to an outer cylindrical portion of the first bearing of the cutter roll, the second pressing mechanism is fixed to an outer cylindrical portion of the second bearing of the cutter roll, and the first servo motor and the second servo motor are rotated in synchronization with each other so as to enable the cutter roll to be separated from the anvil roll.

\* \* \* \* \*